(12) United States Patent
Yang et al.

(10) Patent No.: US 6,468,761 B2
(45) Date of Patent: Oct. 22, 2002

(54) MICROFLUIDIC IN-LINE LABELING METHOD FOR CONTINUOUS-FLOW PROTEASE INHIBITION ANALYSIS

(75) Inventors: Hua Yang, Foster City, CA (US); Steven Sundberg, San Francisco, CA (US)

(73) Assignee: Caliper Technologies, Corp., Mountain View, CA (US)

( * ) Notice: Subject to any disclaimer, the term of this patent is extended or adjusted under 35 U.S.C. 154(b) by 87 days.

(21) Appl. No.: 09/755,608

(22) Filed: Jan. 5, 2001

(65) Prior Publication Data

US 2001/0026929 A1 Oct. 4, 2001

Related U.S. Application Data

(60) Provisional application No. 60/175,142, filed on Jan. 7, 2000.

(51) Int. Cl.[7] .............................. C12Q 1/37; C12Q 1/00; C12M 1/00; C12M 1/34; C12M 1/36
(52) U.S. Cl. ...................... 435/23; 435/24; 435/283.1; 435/287.1; 435/286.1; 435/286.5; 435/4
(58) Field of Search .................. 435/23, 24, 283.1, 435/287.1, 286.1, 286.5, 4

(56) References Cited

U.S. PATENT DOCUMENTS

| | | | |
|---|---|---|---|
| 4,390,403 A | 6/1983 | Batchelder |
| 4,908,112 A | 3/1990 | Pace |
| 5,126,022 A | 6/1992 | Soane et al. |
| 5,296,599 A | 3/1994 | Cohen et al. |
| 5,498,392 A | 3/1996 | Wilding et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,699,157 A | 12/1997 | Parce |

(List continued on next page.)

FOREIGN PATENT DOCUMENTS

| | | |
|---|---|---|
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |

(List continued on next page.)

OTHER PUBLICATIONS

Cohen and Michaud, Analytical Biochemistry 211 (1993) 279–287.
Cohen, C.B. et al., "A Microchip–Based Enzyme Assay for Protein Kinase A," *Anal. Chem.* (1999) 273:89–97.
Dasgupta, P.K. et al., "Electroosmosis: A Reliable Fluid Propulsion System for Flow Injection Analysis," *Anal. Chem.* (1994) 66:1792–1798.

(List continued on next page.)

*Primary Examiner*—Louise N. Leary
(74) *Attorney, Agent, or Firm*—Stacy Landry; Quine Intellectual Property Law Group, P.C.

(57) ABSTRACT

Enzyme assays are performed in microfluidic devices including, e.g., in-line labeling, separation, and detection of assay products. In-line labeling allows assays, e.g., protease assays, to be performed in a continuous flow microfluidic format. Also included are microfluidic devices and integrated systems for performing in-line labeling in continuous flow enzyme assays.

46 Claims, 7 Drawing Sheets

U.S. PATENT DOCUMENTS

| | | | |
|---|---|---|---|
| 5,750,015 | A | 5/1998 | Soane et al. |
| 5,779,868 | A | 7/1998 | Parce et al. |
| 5,800,690 | A | 9/1998 | Chow et al. |
| 5,842,787 | A | 12/1998 | Kopf-Sill et al. |
| 5,852,495 | A | 12/1998 | Parce |
| 5,869,004 | A | 2/1999 | Parce et al. |
| 5,876,675 | A | 3/1999 | Kennedy |
| 5,880,071 | A | 3/1999 | Parce et al. |
| 5,882,465 | A | 3/1999 | McReynolds |
| 5,885,470 | A | 3/1999 | Parce et al. |
| 5,942,443 | A | 8/1999 | Parce et al. |
| 5,948,227 | A | 9/1999 | Dubrow |
| 5,955,028 | A | 9/1999 | Chow |
| 5,957,579 | A | 9/1999 | Kopf-Sill et al. |
| 5,958,203 | A | 9/1999 | Parce et al. |
| 5,958,694 | A | 9/1999 | Nikiforov |
| 5,959,291 | A | 9/1999 | Jensen |
| 5,964,995 | A | 10/1999 | Nikiforov et al. |
| 5,965,001 | A | 10/1999 | Chow et al. |
| 5,965,410 | A | 10/1999 | Chow et al. |
| 5,972,187 | A | 10/1999 | Parce et al. |
| 5,976,336 | A | 11/1999 | Dubrow et al. |
| 5,989,402 | A | 11/1999 | Chow et al. |
| 6,001,231 | A | 12/1999 | Kopf-Sill |
| 6,004,515 | A | 12/1999 | Parce et al. |
| 6,011,252 | A | 1/2000 | Jensen |
| 6,012,902 | A | 1/2000 | Parce |
| 6,042,710 | A | 3/2000 | Dubrow |
| 6,046,056 | A | 4/2000 | Parce et al. |
| 6,068,752 | A | 5/2000 | Dubrow et al. |
| 6,071,478 | A | 6/2000 | Chow |
| 6,074,725 | A | 6/2000 | Kennedy |
| 6,080,295 | A | 6/2000 | Parce et al. |
| 6,197,595 | B1 * | 3/2001 | Anderson et al. ........... 436/180 |

FOREIGN PATENT DOCUMENTS

| | | | |
|---|---|---|---|
| WO | WO 98/46438 | 10/1998 | |
| WO | WO 98/49548 | 11/1998 | |
| WO | WO 98/55852 | 12/1998 | |
| WO | WO 98/56956 | 12/1998 | |
| WO | WO 99/00649 | 1/1999 | |
| WO | WO 99/10735 | 3/1999 | |
| WO | WO 99/12016 | 3/1999 | |
| WO | WO 99/16162 | 4/1999 | |
| WO | WO 99/19056 | 4/1999 | |
| WO | WO 99/19516 | 4/1999 | |
| WO | WO 99/29497 | 6/1999 | |
| WO | WO 99/56954 | 11/1999 | |
| WO | WO 99/64848 | 12/1999 | |
| WO | WO 00/09753 | 2/2000 | |
| WO | WO 01/02850 | 1/2001 | |
| WO | WO 01/14064 | 3/2001 | |

OTHER PUBLICATIONS

Jacobson, S.C. et al., "Fused Quartz Substrates for Microchip Electrophoresis," *Anal. Chem.* (1995) 67–2059–2063.

Jacobson, et al. Anal. Chem. 66 (1994) 3472–3476.

Krull, et al., J. Chromatogr. 699 (1997) 173–208.

Manz, A. et al., "Electroosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip." *Anal. Chem.* (1994) 66:3485–3491.

Sundberg, S. A., "High–throughput and ultra–high–throughput screening: solution—and cell–based approches," *Current Opinions in Biotechnology* 2000, 11:47–53.

* cited by examiner

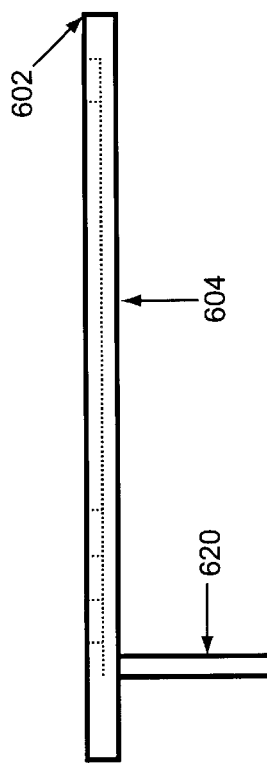
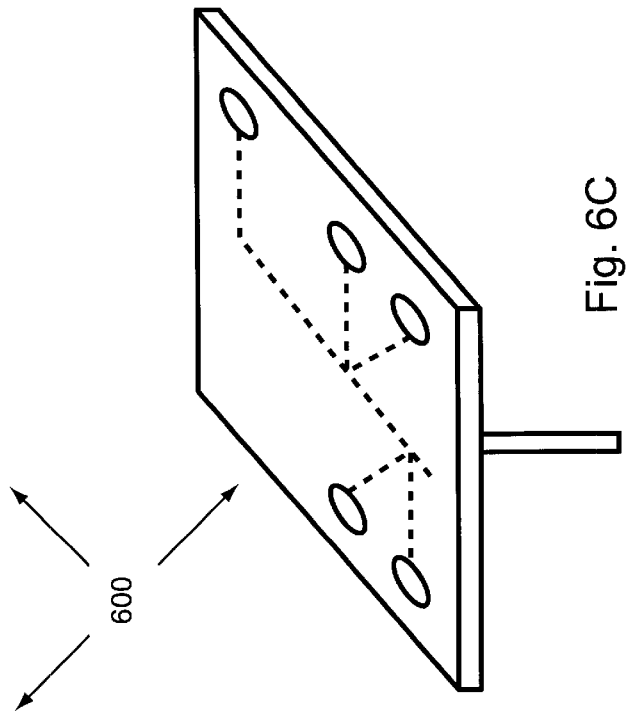
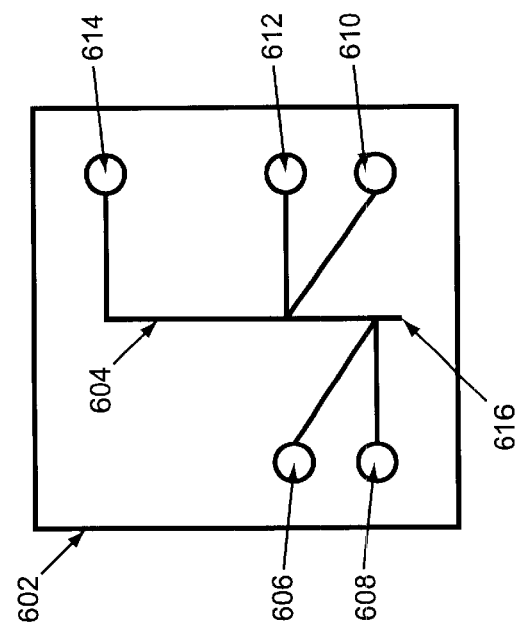
Fig. 6B
Fig. 6C
Fig. 6A

MICROFLUIDIC IN-LINE LABELING METHOD FOR CONTINUOUS-FLOW PROTEASE INHIBITION ANALYSIS

CROSS-REFERENCE TO RELATED APPLICATIONS

Pursuant to 35 U.S.C. §119(e) and any other applicable statute or rule, the present application claims benefit of and priority to U.S. Ser. No. 60/175,142 entitled "Microfluidic In-line Labeling Method for Continuous-Flow Protease Inhibition Analysis," filed Jan. 7, 2000 by Yang and Sundberg.

BACKGROUND OF THE INVENTION

There is considerable interest by biochemists, clinical chemists, pharmaceutical manufacturers, and other scientists in determining the concentration of amino acids, peptides, and other amine-functional compounds in complex biological samples. This analysis currently requires the detection of a plurality of compounds with a high degree of sensitivity and detection selectivity. Typical detection schemes involve, e.g., the use of fluorescent tags on the compounds of interest. A common method is to convert the compounds of interest into a derivative with a strong fluorescence signal. The derivatizing agent affects the ultimate sensitivity and accuracy of the analysis. Thus, a derivatizing reagent that maximizes sensitivity, yield, and stability of the derivatized amino acids is desired.

Many such derivatives have been studied, including heterocyclic aromatic carbamate compounds and aromatic dialdehydes. See, e.g., U.S. Pat. No. 5,296,599 issued Mar. 22, 1994 by Cohen and Michaud, Analytical Biochemistry, Cohen and Michaud, 211 (1993) 279–287, Jacobsen et al., Anal. Chem. 66 (1994) 3472–3476 and Krull et al., J. Chromatogr. 699 (1997) 173–208. Jacobsen, for example, describes the use of o-phthaldialdehyde for fluorescently tagging amino acids and Cohen describes the use of 6-aminoquinolyl-N-hydroxysuccinimidyl carbamate for labeling amino acids, peptides, and proteins.

The studies described above are typically performed in conjunction with chromatographic separation and detection. Improved methods for studying and detecting amino acids, peptides, and the like, are desired, e.g., improved methods for performing assays in microfluidic devices. Microfluidic devices useful in such methods have been described by the inventors and their coworkers in various publications, published PCT applications, and U.S. patent applications.

Improvements to such devices and methods would be desirable. For example, a method of labeling assay components in a microfluidic device would be useful. The methods and devices of the present invention provide these features and many others that will be apparent upon complete review of the following.

SUMMARY OF THE INVENTION

The present invention provides microfluidic methods, devices and systems for performing in-line labeling for continuous-flow assays, e.g., protease inhibition assays. For example, a protease assay is performed using unlabeled, e.g., non-fluorogenic substrates, and then the products are labeled using fast amino derivatization chemistry. Due to the fast derivatization, the labeling step is performed as the products are produced and/or flowed through the system. The method therefore provides a rapid, one step labeling procedure that forms stable derivatives that are readily amenable to separation, analysis, and detection. The products are optionally separated either before, or after, the labeling step.

In one aspect, the present invention provides a method of labeling a reaction product in a microfluidic system, e.g., when performing a protease assay, e.g., an inhibition assay. The method comprises flowing a protease through a microscale cavity and contacting the protease with a protease substrate. Other reagents are optionally mixed into the enzymatic reaction, e.g., modulators, inhibitors, activators, and the like. The protease acts on the protease substrate, e.g., in the presence of an inhibitor or modulator, to form products, e.g., amino acids, peptides, or proteins. The products are then labeled with a labeling reagent, thus producing labeled products. The labeled products are typically detected, e.g., fluorescently detected, and analyzed, e.g., quantitated.

The labeling step includes chemically reacting the products with a labeling reagent, which is typically an amine-derivatizing reagent, e.g., a heterocyclic aromatic carbamate compound or an aromatic dialdehyde.

Heterocyclic aromatic carbamate compounds include 6-aminoquinolyl-N-hydroxysuccinimidyl carbamate, 3-aminoquinolyl-N-hydroxysuccinimidyl carbamate, 5-aminoquinolyl-N-hydroxysuccinimidyl carbamate, 5-aminoisoquinolyl-N-hydroxysuccinimidyl carbamate, 6-amino-4-methylquinolyl-N-hydroxysuccinimidyl carbamate, 6-amino-2,4-dimethylquinolyl-N-hydroxysuccinimidylcarbamate, 6-amino-2phenylquinolyl-N-hydroxysuccinimidyl-carbamate, 6-amino-2-methoxy-4-methylquinolyl-N-hydroxysuccinimidylcarbamate, 4-aminoquinaldine-N-hydroxysuccinimidyl carbamate, 9-aminoacridine-N-hydroxysuccinimidyl carbamate, 2-aminoacridine-N-hydroxysuccinimidylcarbamate, luminol-N-hydroxysuccinimidylcarbamate, isoluminol-N-hydroxysuccinimidylcarbamate, 7-amino-4-methylcoumarin-N-hydroxysuccinimidylcarbamate, 7-amino-4-(trifluoromethyl)coumarin-N-hydroxysuccinimidylcarbamate, 4'-(aminomethyl)fluorescein-N-hydroxysuccinimidylcarbamate, 5-(aminomethyl)fluorescein-N-hydroxysuccinimidylcarbamate, 5-aminoeosin-N-hydroxysuccinimidylcarbamate, Cascade Blue ethylenediamine-N-hydroxysuccinimidylcarbamate, and the like.

Aromatic dialdehydes include o-pthaldialdehyde, napthalene-2-3-dicarboxaldehyde, anthracene-2,3-dicarboxaldehyde, and the like. Other amine-derivatizing reagents useful in the present invention include 3-(4-carboxybenzoylquinoline-2-carboxaldehyde, 3-(2-furosyl)quinoline-2-carboxaldehyde, fluorescamine, 7-nitrobenz-2-oxa-1,3-diazole chloride, and the like.

In some embodiments, the methods of the present invention also involve separating the products before or after the labeling step. Separation comprises electrophoretically separating the various components in a polymer, a gel, a solution, or the like, e.g., polyacrylamide, polydimethylacrylamide/co-acrylic acid, or other separation matrices or polymers.

In other embodiments, the methods include flowing an inactivating reagent through the microscale cavity after the labeling step, thereby inactivating any labeling reagents that have not reacted with the products. For example, the inactivating reagent is optionally one that alters the pH of the materials or fluids in the microscale cavity.

In another aspect, the present invention provides devices and systems for performing the above assays and labeling reactions. The devices comprise a body structure having microscale channels disposed therein. The channels typically include a main channel, in which a protease and a protease substrate are combined to form one or more products, and a labeling channel region fluidly coupled to the main channel, in which the products are labeled. Also included are (a) detection channel region(s) fluidly coupled to the main channel, for detecting the labeled products, and sources for the components and reagents. Such sources include, but are not limited to, sources for labeling reagents, proteases, protease substrates, inactivating reagents, and the like. In addition, the device typically comprises a labeling reagent, e.g., an amine-derivatizing reagent such as those listed above. Separation channels, e.g., a channel comprising a polymer, gel, or solution, e.g., of polyacrylamide or polydimethylacrylamide/co-acrylic acid, are also optionally included in the above devices.

Systems incorporating the above devices are also provided. Such systems are used to perform assays or labeling reaction as described above. The systems typically include a fluid direction system operably coupled to the microfluidic device for transporting components, materials, enzymes, reagents, and the like through the plurality of microscale channels. Control systems are provided in the systems for instructing the fluid direction system to transport the reagents and a detection system is provided to detect the reagents. Computers and software are also optionally coupled to the system. Software for performing assays in the systems of the invention typically includes at least one instruction set to analyze signals produced from the detection system, quantitate signals produced from the detection system, and/or direct fluid movement in the system.

BRIEF DESCRIPTION OF THE FIGURES

FIG. 6: Panels A, B, and C are schematic drawings of an integrated system of the invention, including a body structure, microfabricated elements, and a pipettor channel.

FIG. 7: Schematic drawing of an integrated system of the invention further depicting incorporation of a microwell plate, a computer, detector and a fluid direction system. The integrated system is optionally used with either the device or body structure of FIGS. 1, 2, 3, or the like.

DETAILED DISCUSSION OF THE INVENTION

Figure 1:
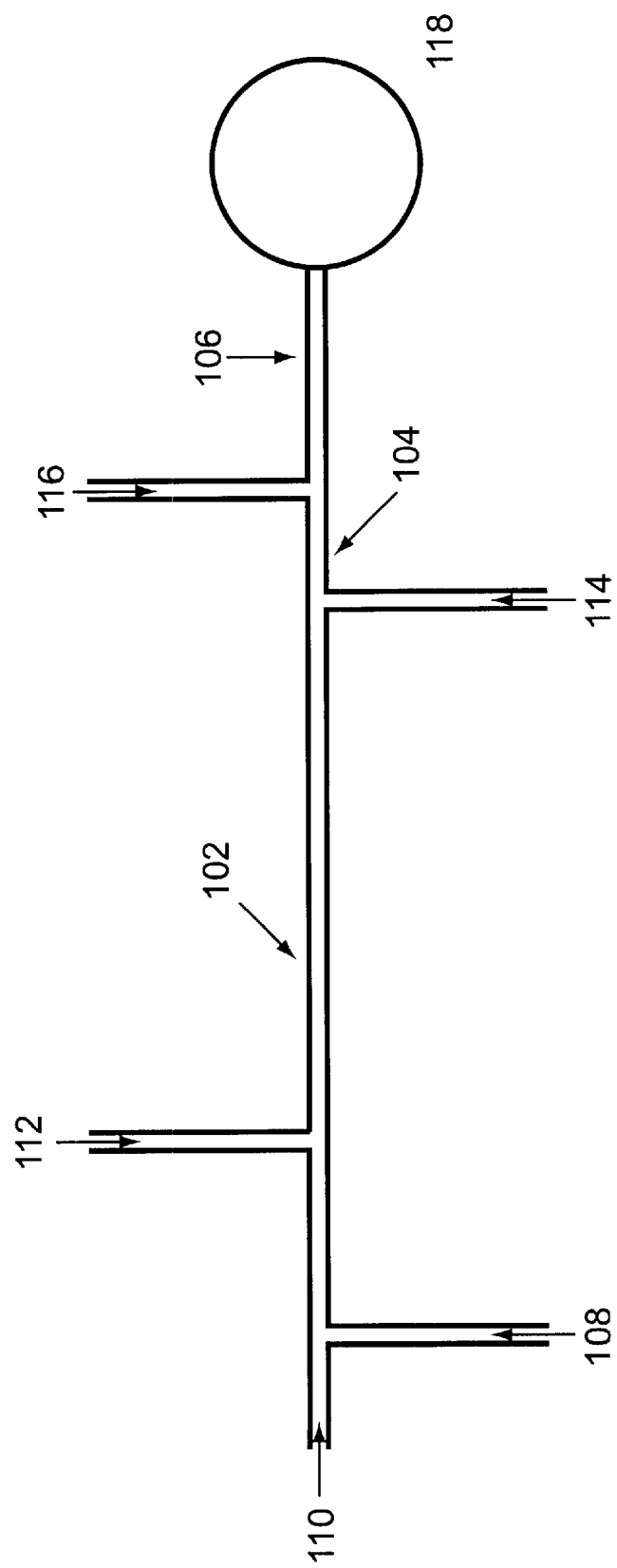
FIG. 1: A schematic illustration of a device for performing in-line labeling of products in a protease assay.

The present invention provides an in-line method of labeling reagents and/or products within a microfluidic device. Therefore, the invention provides methods for continuous flow protease assays to be performed on unlabeled substrates. The system provides fast amino-derivatization chemistry, thus allowing high-throughput assays to be performed on unlabeled substrates, e.g., non-fluorogenic substrates.

The method typically involves performing an enzymatic reaction on unlabeled substrates in a microfluidic system. The products of the reaction are then labeled using a labeling reagent. The labeling reagent chemically reacts with the products to provide a fluorescent derivative. The derivative is typically easily detectable, stable, and pure, i.e., only one form of the derivative is typically produced. Useful derivatives include, but are not limited to, heterocyclic aromatic carbamate compounds and aromatic dialdehydes.

The labeled products produced by the derivatization are optionally separated before or after the labeling reaction, typically by electrophoretic separation. After separation and labeling, the fluorescent tags applied to the products in the labeling reaction are optionally used to detect the products. Further analysis, e.g., concentration measurements, kinetic studies, and the like are also optionally performed on the labeled products, e.g., in an integrated system which includes a computer and appropriate software for performing the analysis.

I. Microfluidic Devices Useful in Performing In-line Labeling

The microfluidic devices of the present invention are used to perform continuous-flow protease assays incorporating in-line labeling. The devices generally comprise a body structure with microscale channels or other cavities fabricated therein. For example, the present system comprises one or more of: a main microscale cavity, a labeling region, a detection region, a separation region, and reagent sources. The reagent sources are typically reservoirs or wells for adding, removing, or storing the various reagents of interest. In some embodiments, the device comprises a selected reagent, e.g., an amine-derivatizing reagent, which is typically contained within one of the reagent sources.

The main channel of the present devices is typically a microscale cavity fabricated within the body structure. The main channel or microscale cavity is used, e.g., to mix two or more reagents, to react two or more reagents, to dilute reagents, to separate various components, and the like. Typically, the reservoirs or sources of reagents are fluidly coupled to the main channel so that reagents are optionally introduced into the main channel from the reservoirs.

Various channel regions are contained within or branch out from the main channel. For example, a labeling channel region is optionally positioned within the main channel or in a channel intersecting or otherwise being fluidly connected to the main channel. Various reagents, e.g., proteins, peptides, amino acids, nucleotides, and the like, are optionally labeled in a labeling region within the main channel. Alternatively, a labeling channel or channel region is provided that intersects the main channel.

A detection region is typically included in the devices of the present invention for the detection of labeled compounds. For example, the compounds labeled in the labeling region, e.g., fluorescently labeled peptides or amino acids, are transported from the labeling region into a detection region, where they are detected with, e.g., a fluorescent detector.

The detection region is optionally a subunit of a channel, or it optionally comprises a distinct channel that is fluidly coupled to the plurality of channels in the microfluidic device, e.g., to the main channel. The detection region typically includes a window at which a signal is monitored. The window typically includes a transparent cover allowing visual or optical observation and detection of the assay results, e.g., observation of a colorimetric or fluorometric signal or label. Examples of suitable detectors are well known to those of skill in the art and are discussed in more detail below.

In addition to the above channel regions, the devices of the present invention optionally include a separation region or a separation channel. Mixtures of components are separated into their various components as they are flowed through a separation channel. The separation region or channel is typically a polymer, gel, or separatory solution filled channel. For example, the channel optionally comprises polyacrylamide or polydimethylacrylamide/co-acrylic acid in polymer, solution, or gel form. In a polyacrylamide filled channel, components are separated based on the charge/mass ratio of each of the components. Different components elute from the separation channel with different retention times. Molecular weight is optionally determined from the retention time of the various components. In the present invention, a separation region is typically used to separate components in a reaction mixture, e.g., a substrate from a product, or the components of a mixture of peptides and/or amino acids.

The above channel regions are fluidly coupled to each other and to various pressure sources and/or electrokinetic sources. Fluidic materials, such as protease solutions, i.e., solutions comprising protease enzymes, substrate solutions, labeling reagents, and the like, are typically transported through the interconnected channel system by the application of pressure and/or electrokinetic forces to the fluid materials in the channels. Therefore, various pressure sources and electrokinetic controllers are optionally coupled to the devices of the invention.

Typically, the pressure sources are applied at channel ends. For example a waste well is optionally placed at one end of a main channel with a sample source at the other end. A pressure source applied at the waste well is optionally used to draw fluid into the channel. For example, a vacuum source may be fluidly coupled to the device at a waste reservoir located at the end of a deep mixing channel. Additionally, the vacuum optionally draws any excess, or unused material, e.g., material not injected into a separation channel, into the waste reservoir to which the vacuum source is fluidly coupled. Alternatively, a positive pressure source is fluidly coupled to a sample well or reservoir at one end of a main channel. The pressure then forces the material into and through the main channel. The vacuum source draws fluid into the main channel for mixing or reacting with other reagents.

Alternatively, electrokinetic forces, e.g., high or low voltages, are applied at reservoirs to introduce materials into the channels or transport materials through the channels. For example, voltage gradients applied across a separation channel are used to move fluid down the channel, thus separating the components of the material as they move through the channel at different rates.

Sources of materials are also typically placed in fluid communication with the microfluidic channels and the pressure or electrokinetic voltage sources. Such sources are typically wells or reservoirs for, e.g., storing, introducing, and removing components from or into the device. For example, a sample, e.g., an inhibitor, is optionally placed in a reservoir in the device. From the reservoir, the sample is optionally introduced into the device and flowed into contact with an enzyme and substrate for reaction. Waste wells are used in the devices, e.g., at the end of a main channel, to discard or reuse reagents and components at the conclusion of an assay. Such sources optionally comprise one or more of the following: enzymes, e.g., proteases, substrates, e.g., proteins or peptides, modulators, e.g., inhibitors or activators, inactivating reagents, e.g., an acidic or basic solution, labeling reagents, e.g., amine-derivatizing reagents, waste products, or the like. Introduction of these elements into the system is carried out as described below.

Figure 4:
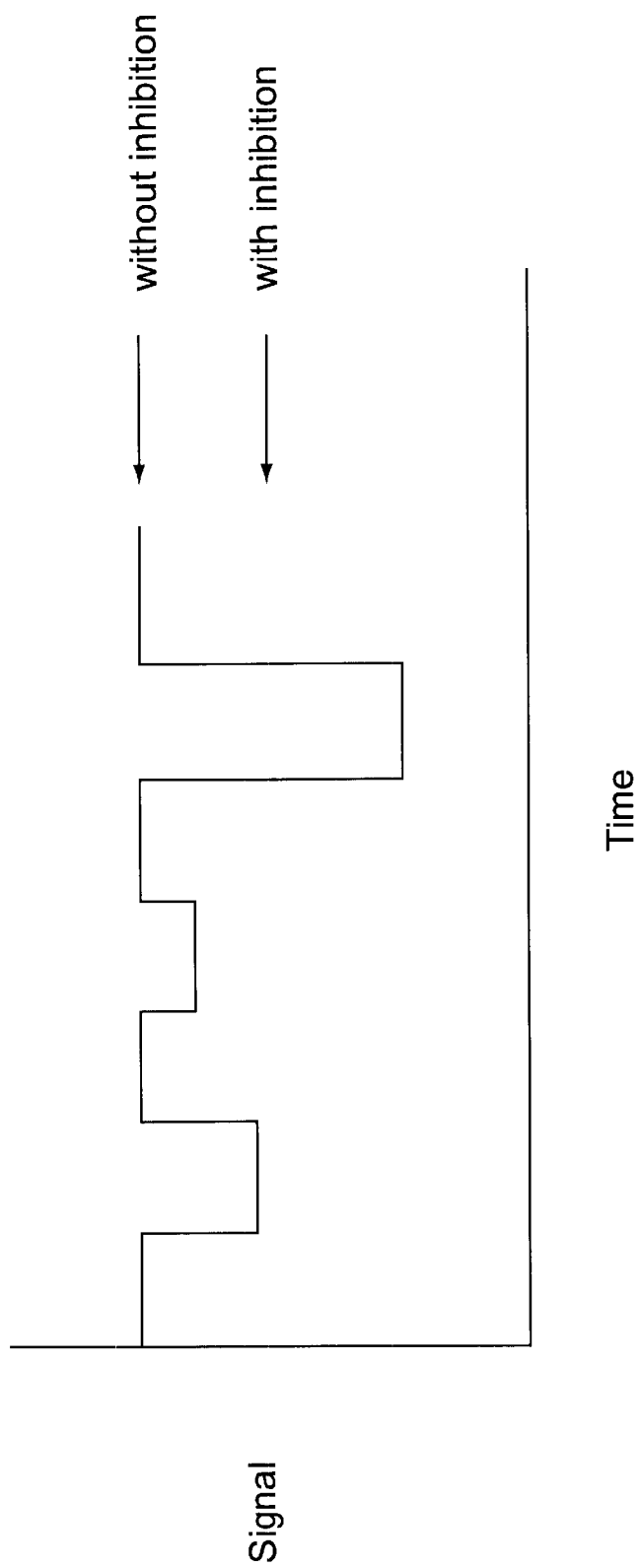
FIG. 4: A schematic representation of data obtained from a protease reaction performed using the methods and devices of the invention.

One embodiment of the present devices is illustrated in FIG. 1. As shown, the system comprises main channel 102. To perform an assay, e.g., a protease assay, various reagents are added into main channel 102. For example, a sample, e.g., a potential protease modulator, such as a protease inhibitor or activator, is introduced into main channel 102 from a reservoir, e.g., inhibitor source 110. Other reagents used in the reaction of interest are introduced into main channel 102 also, e.g., from an internal reservoir or well disposed within the body structure of the device or from an external source such as a capillary or pipettor fluidly coupled to the device and to a source of reagents. In a protease assay, for example, a protease and protease substrate are introduced into main channel 102 from, e.g., source 108 and/or source 112. The protease and substrate react in the presence of the modulator to form products. When the modulator serves as an inhibitor the amount of product is reduced in comparison to the amount produced without the presence of the inhibitor. As shown in FIG. 4, the amplitude of the signal is reduced in the presence of an inhibitor. After the reaction takes place between the various reagents, the products are flowed through labeling region 104. A labeling reagent is introduced into the device, e.g., through reservoir or source 114, and into labeling region 104 to contact the products. A reaction between the products and the labeling reagent produces labeled products. The labeled products are then optionally contacted with an inactivating reagent. The inactivating reagent is optionally added into labeling region 104 through source 116. The inactivating reagent reacts with any unreacted labeling reagent, thus reducing background signal levels. The labeled products are typically flowed through detection region 106, in which the products are detected, e.g., by fluorescence detection.

Figure 2:
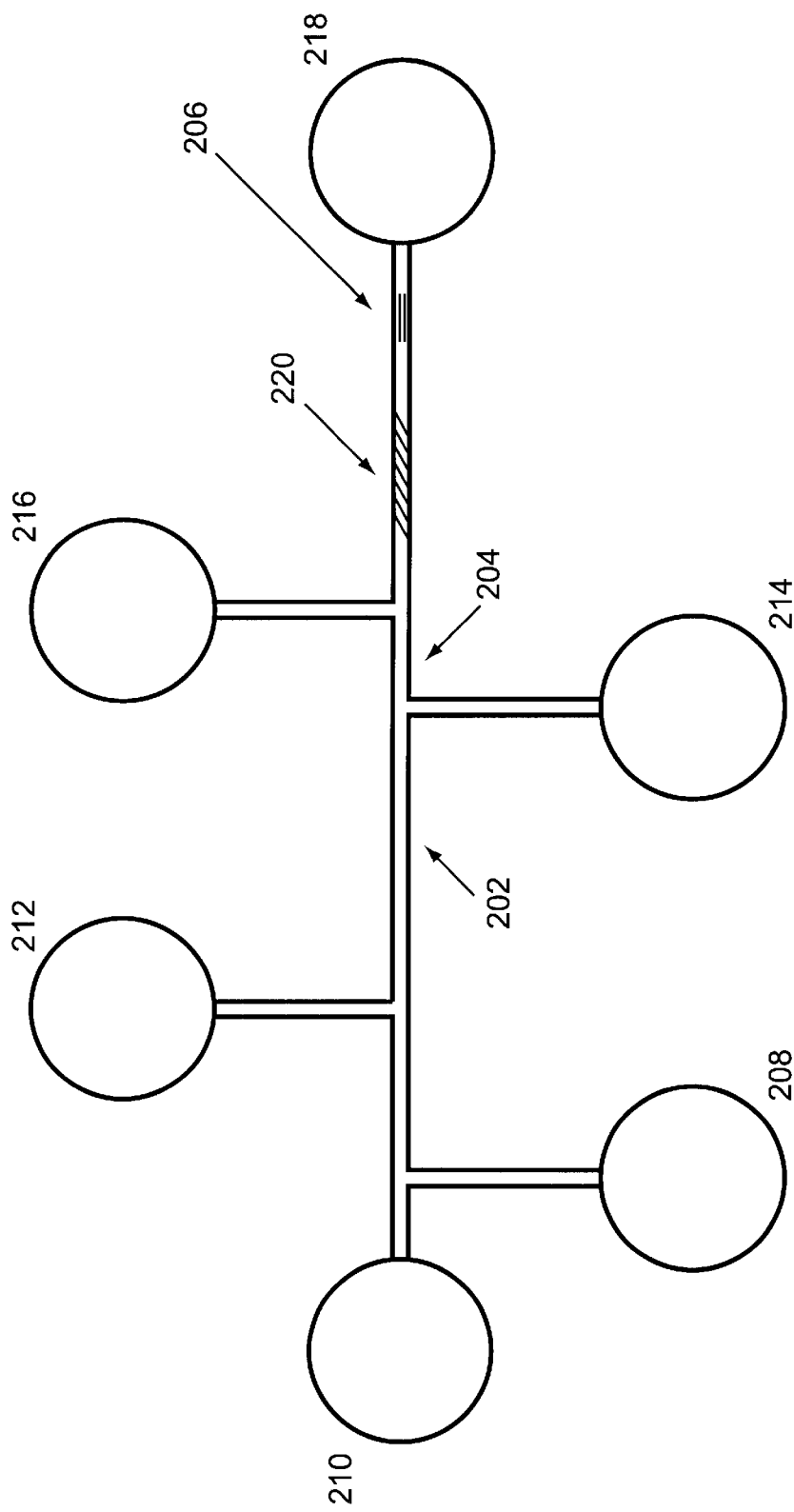
FIG. 2: Schematic illustration of an alternate device for performing in-line labeling of products, e.g., in a protease reaction. This device includes a separation channel region for separating mixtures of products after they have been labeled.

An alternative device is provided in FIG. 2. The device in FIG. 2 provides separation channel region 220. Reagents are introduced into and reacted in the channels of FIG. 2 in substantially the same way as those in FIG. 1 described above. The reagents are added into main channel 202, e.g., through reservoirs 210, 208, and 212 and reacted in main channel 202. Labeling of the products occurs through a chemical reaction with the labeling reagent, which is optionally contained within reservoir 214, when it is flowed into labeling channel region 204. An inactivating reagent is optionally added, e.g., through reservoir 216, to decrease background signal as described above. After labeling, the products are optionally separated in separation channel region 220 and detected in detection channel region 206.

Figure 3:
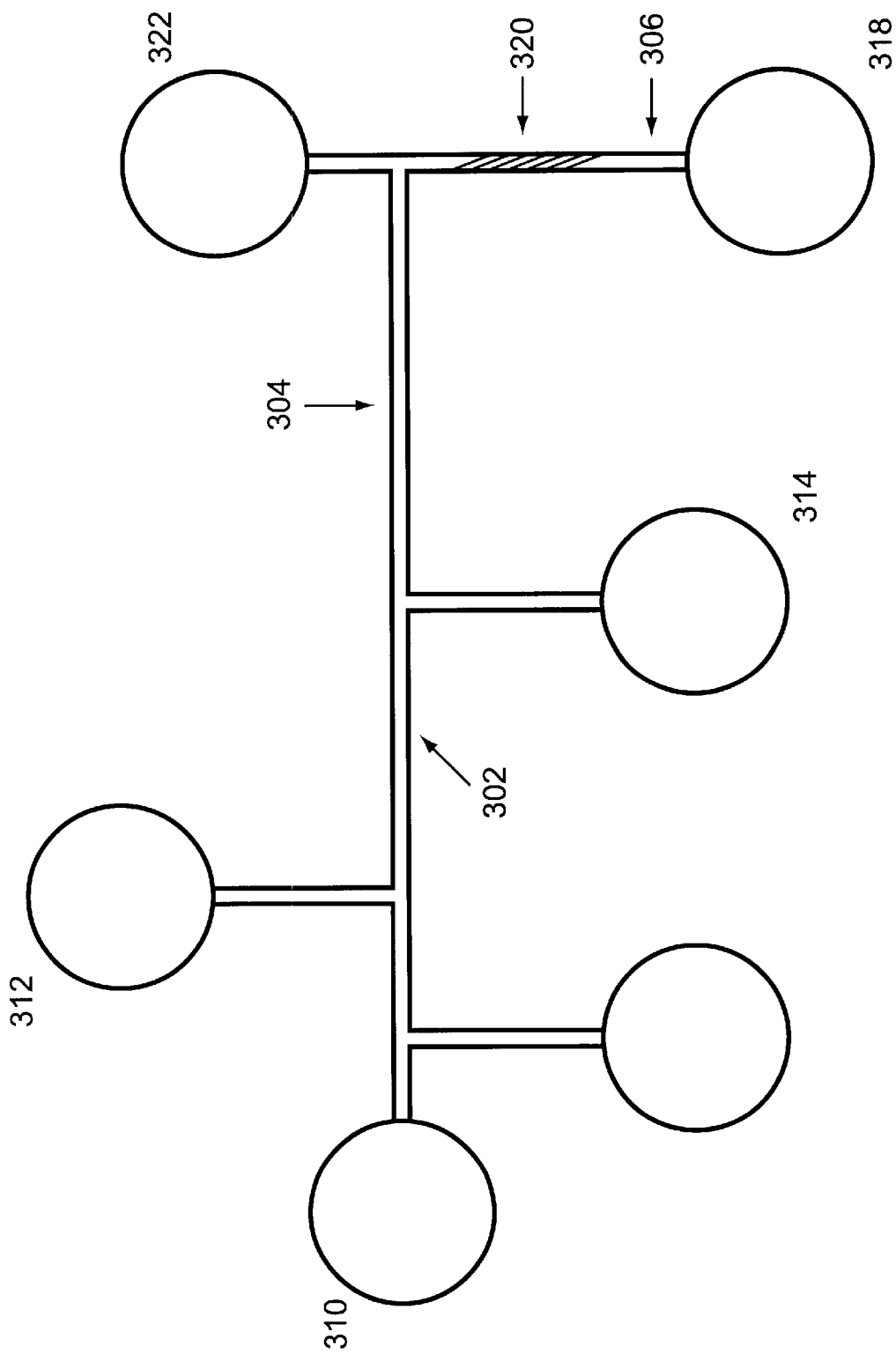
FIG. 3: Schematic illustration of an alternate channel configuration for performing the assays of the invention. The device includes a distinct separation channel.

Alternatively, the products are injected into a distinct separation channel, such as separation channel 320 in FIG. 3. Samples, reagents, and the like are optionally added into the device from reservoirs 310, 312, 308, 314, and the like, and reacted in main channel 302. For example, the products resulting from a reaction in main channel 302 and a labeling reaction in labeling region 304 are optionally injected into separation channel 320. For example, a cross injection using voltages at reservoirs 322 and 318 injects the volume of fluid at the intersection of main channel 302 and separation channel 320 into separation channel 320. In separation channel 320, a mixture of components, e.g., of proteins peptides, or amino acids, is separated, e.g., by electrophoresis. A detector is optionally positioned proximal to detection region 306 to detect the components as they elute from separation channel 320. When the assay and detection are complete, the sample components are optionally directed to reservoir 318 for disposal or retrieval. A variety of substantially similar configurations will be apparent to one of skill upon full consideration of the foregoing and following descriptions.

II. Protease Assays Performed Using the Methods and Devices of the Invention

To perform an enzyme assay, a substrate, e.g., a protein, is mixed with or otherwise contacted by an enzyme. The enzyme catalyzes a reaction with the substrate, thus forming products, such as protease cleavage products. Typically, the reaction is carried out in the presence of a modulator, e.g., an inhibitor or activator. In the present invention, assays, such as a protease inhibition assay, are typically performed in a continuous-flow format in the microscale channels of a microfluidic device. Therefore the present invention includes methods for flowing the assay reactants through the microscale channels of the devices.

Typically, the reactants move through the channels due to the application of pressure or electrokinetic forces as described above. When two reactants are introduced into the same channel, the two reactants mix and contact each other to react and form products. For example, a protease is optionally flowed through a microfluidic channel under pressure. The protease is then contacted by or mixed with a substrate. The protease and substrate combine and form products, e.g., cleaved protein fragments.

Typically, the assays of the invention are protease assays. "Proteases" are enzymes that degrade proteins by hydrolyzing peptide bonds between amino acid residues. They are also known as proteinases. Categories of proteases include thiol proteases, acid proteases, serine proteases, and the like. Example proteases include, but are not limited to, carboxypeptidase A, subtilisin, papain, and pepsin. "Protease substrates" of the present invention include, but are not limited to, proteins, peptides, and the like. In the present invention, the substrates are unlabeled, e.g., non-fluorogenic substrates. A protease catalyzes the hydrolysis of a protease substrate, e.g., a protein or polypeptide, producing degraded protein products. The term "products," as used herein, refers to the compounds or components produced by an assay or reaction, e.g., in the main channel of the microfluidic device. Typically, the products are the results of an enzyme-catalyzed reaction, e.g., a protease reaction. For example, a protease hydrolyzes peptide bonds in proteins resulting in peptides and amino acids as products. The products of the invention, therefore include, but are not limited to, peptides, polypeptides, amino acids, protein fragments, and the like.

In the present invention, because the substrates used are typically non-labeled substrates, the products produced are typically unlabeled products. For example, a protein is hydrolyzed to form a variety of peptides in a reaction catalyzed by a protease. If a labeled protein is used, one or more of the resulting peptides will retain the label. When an unlabeled protein is used, the resulting peptides or amino acids are also unlabeled.

Various characteristics of protease reactions are studied using protease assays. For example, enzyme mechanisms, kinetics, and inhibition are studied using protease assays. A protease inhibition assay provides, e.g., information on the types of compounds that inhibit proteases and the level of inhibition they provide.

Modulators, e.g., inhibitors or activators, are compounds that affect the ability of an enzyme to catalyze a reaction (positively or negatively). For example, an inhibitor inhibits or curbs enzyme activity. For example, pepstatin acts as a protease inhibitor by inhibiting the activity of carboxyl proteases. An activator increases or improves enzyme activity, e.g., compared to enzyme activity when the activator is not present. Many drugs and toxic agents act by inhibiting the ability of an enzyme to catalyze a reaction. Therefore, the study of enzyme inhibition, e.g., protease inhibition, is of great interest. The present invention provides methods of performing protease inhibition assays in a continuous flow format. The system allows many inhibitor samples to be tested in a short amount of time, e.g., in a high-throughput-system. Modulators are optionally added before, during, or after the enzyme and substrate are contacted, depending on the format of the assay.

For example, to perform a protease inhibition assay using the methods of the present invention, a potential inhibitor is introduced into a microscale channel in which a protease reaction is carried out. The protease reaction proceeds in the presence of the potential inhibitor and produces hydrolyzed products, e.g., degraded proteins or peptides. For example, a potential inhibitor compound is optionally sipped, e.g., through an external capillary, from a microtiter plate containing a plurality of samples. The plurality of samples optionally comprises potential modulators, inhibitors, and/or activators. The potential inhibitor is typically introduced into the microscale channel in which the protease substrate and protease are located. The potential inhibitor mixes with the other components of the reaction mixture and the reaction proceeds in the presence of the potential inhibitor. The substrate is hydrolyzed or partially hydrolyzed, e.g., depending on the level of inhibition, and the products, e.g., the amount of product produced in the presence of the potential inhibitor, are typically detected, e.g., to determine the level of inhibition or activation of the sample.

Labeling the Products of a Protease Assay

After a substrate, e.g., a protein, peptide, or antibody, is hydrolyzed, e.g., by a protease in an enzyme assay, the products, e.g., peptides, polypeptides, or amino acids, are typically detected. To detect the products, a label, e.g., a fluorescent tag, is generally used. For example, a fluorescent label is optionally attached to an enzyme substrate. Upon reaction, the substrate yields a labeled product, which is detected, e.g., by fluorescence. The present invention provides a method of performing an assay using non-labeled substrates, e.g., non-fluorogenic substrates.

Instead of labeling substrates, the present invention provides methods for labeling the assay products. Furthermore, the labeling step is performed in-line in a microfluidic device after the assay is complete. The labeling step is generally carried out in solution, in the microfluidic device, without pre-concentration or removal of the components from the system, although these steps are optionally performed as well. Furthermore, the reaction is optionally carried out in a complex biofluid, e.g., blood, serum, cell extracts, or the like.

After the enzyme, e.g., a protease, is contacted with a substrate, and optionally, a modulator, a labeling reagent is added to the products formed from the enzyme catalyzed reaction. Alternatively, the labeling regent is added to the reaction mixture concurrent with the reaction. The products of the enzymatic reaction react with the labeling reagent to form labeled products. The labeling-reagents of the present invention react with the products to tag reactive amine groups with a fluorescent tag.

The labeling reagent is typically an amine-derivatizing reagent, e.g., a heterocyclic aromatic carbamate compound or an aromatic dialdehyde. These derivatizing reagents chemically react with amine groups to form labeled products, e.g., products comprising a fluorescent tag or label. The reaction results in a chemical modification of the original product, e.g., of the peptide, protein, or amino acid.

"Chemically reacting," as used herein, refers to a modification that changes or modifies the chemical structure of the product, e.g., to provide a fluorescent label. The modification or change to the product is generally one of two types: (1) the addition of another reagent to the structure, e.g., a protein or peptide chain or carbohydrate site of antibodies, or (2) a molecular rearrangement of atoms somewhere within the product induced by, e.g., thermal, photochemical, radiolytic, or other methods. For example, the labeling reaction optionally tags, derivatizes, or modifies the original product, e.g., by the addition of one or more reagents to the original protein backbone. Typically, the addition of the reagent provides a detectable label to the product, e.g., a fluorescent label.

Typically, the labeling reagent selectively tags or labels reaction products, e.g., proteins, peptides, antibodies, amino acids, or the like, using pre-separation or post-separation labeling. The labeling optionally occurs at trace concentration levels and tags a protein or peptide at a specific site, e.g., a reactive amino site. Preferably, the labeling reaction results in labeled products having the same number of tags all at the very same sites with a conversion of about 80%, preferably about 90%, and more preferably about 100%. In addition, the labeling reaction is preferably carried out in a rapid fashion, on the order of seconds or minutes.

A typical labeling reagent in the present invention is an amine-derivatizing reagent, which modifies, tags, or derivatives a product at a reactive amine site. Examples of types of amine-derivatizing reagents include, but are not limited to, heterocyclic aromatic carbamate compounds, aromatic dialdehydes, and the like. In some embodiments, the amine-derivatizing reagent is essentially a non-fluorescent reagent prior to reacting the labeling reagent, e.g., the amine-derivatizing reagent, with the one or more products, e.g., prior to reaction with the amine. The reaction with the amine typically produces a fluorescent product. For more detailed descriptions of available reagents, see, e.g., Jacobsen et al., Anal. Chem. 66 (1994) 3472–3476 and Krull et al., J. Chromatogr. 699 (1977) 173–208.

Heterocyclic aromatic carbamate compounds have been described by Cohen and Michaud, e.g., in U.S. Pat. No. 5,296,599 issued Mar. 22, 1994 and in *Analytical Biochemistry*, 211 (1993) 279–287. These compounds typically act as amine-derivatizing reagents for proteins, peptides, and amino acids. An example reaction is presented in FIG. 5, in which a substrate, e.g., a peptide, protein, or the like, is mixed with an enzyme, e.g., a protease, to form products, e.g., peptides, amino acids, and the like. Labeling reagent is optionally added to produce a fluorescent product and inactivating reagent is optionally added to inactivate any unreacted labeling reagent, e.g., fluorescamine. Heterocyclic aromatic carbamate compounds are optionally used in the present invention as labeling reagents to form chemical derivatives useful in the analysis and purification of amines, e.g., to label and separate mixtures of amino acids and peptides. The derivatives are prepared with high purity, e.g., no fluorescent impurities, via a rapid and high-yielding chemical reaction. In addition, the derivatives are stable for a long enough period to allow separation and/or analysis, such as concentration measurements on the various labeled products or derivatives. For example, the fluorescent derivatives formed by reaction with the heterocyclic aromatic carbamate compounds listed below are formed within minutes of adding the derivatizing reagent and are stable in solution for about 14 days.

The heterocyclic aromatic moiety of the derivatizing reagents of the invention is optionally any aromatic ring structure, including polycyclic structures, typically containing from about 1 to about 4 heteroatoms such as nitrogen, oxygen, sulfur, and combinations thereof. One or multiple heteroatoms is optionally present outside the ring structure and include nitrogen, oxygen, sulfur, halogens, and combinations thereof. The heterocyclic moiety is optionally substituted with a non-reactive electron-donating group, such as alkyl, alkoxy, or aromatic groups. For example, the heterocyclic aromatic amine is optionally aminoquinoline, substituted aminoquinoline, aminoisoquinoline, aminocoumarin, aminoacridine, or the like.

Heterocyclic aromatic carbamate compounds include, but are not limited to, 6-aminoquinolyl-N-hydroxysuccininimydyl carbamate, 3-aminoquinolyl-N-hydroxysuccinimidyl carbamate, 5-aminoquinolyl-N-hydroxysuccinimidyl carbamate, 5-aminoisoquinolyl-N-hydroxysuccinimidyl carbamate, 6-amino-4-methylquinolyl-N-hydroxysuccinimidyl carbamate, 6-amino-2,4-dimethylquinolyl-N-hydroxysuccinimidylcarbamate, 6-amino-2-phenylquinolyl-N-hydroxysuccinimidy-lcarbamate, 6-amino-2-methoxy-4-methylquinolyl-N-hydroxysuccinimidylcarbamate, 4-aminoquinaldine-N-hydroxysuccinimidyl carbamate, 9-aminoacridine-N-hydroxysuccinimidyl carbamate, 2-aminoacridine-N-hydroxysuccinimidylcarbamate, luminol-N-hydroxysuccinimidylcarbamate, isoluminol-N-hydroxysuccinimidylcarbamate, 7-amino-4-methylcoumarin-N-hydroxysuccinimidylcarbamate, 7-amino-4-(trifluoromethyl)coumarin-N-hydroxysuccinimidylcarbamate, 4'-(aminomethyl)fluorescein-N-hydroxysuccinimidylcarbamate, 5-(aminomethyl)fluorescein-N-hydroxysuccinimidylcarbamate, 5-aminoeosin-N-hydroxysuccinimidylcarbamate, and Cascade Blue ethylenediamine-N-hydroxysuccinimidylcarbamate.

Figure 5:
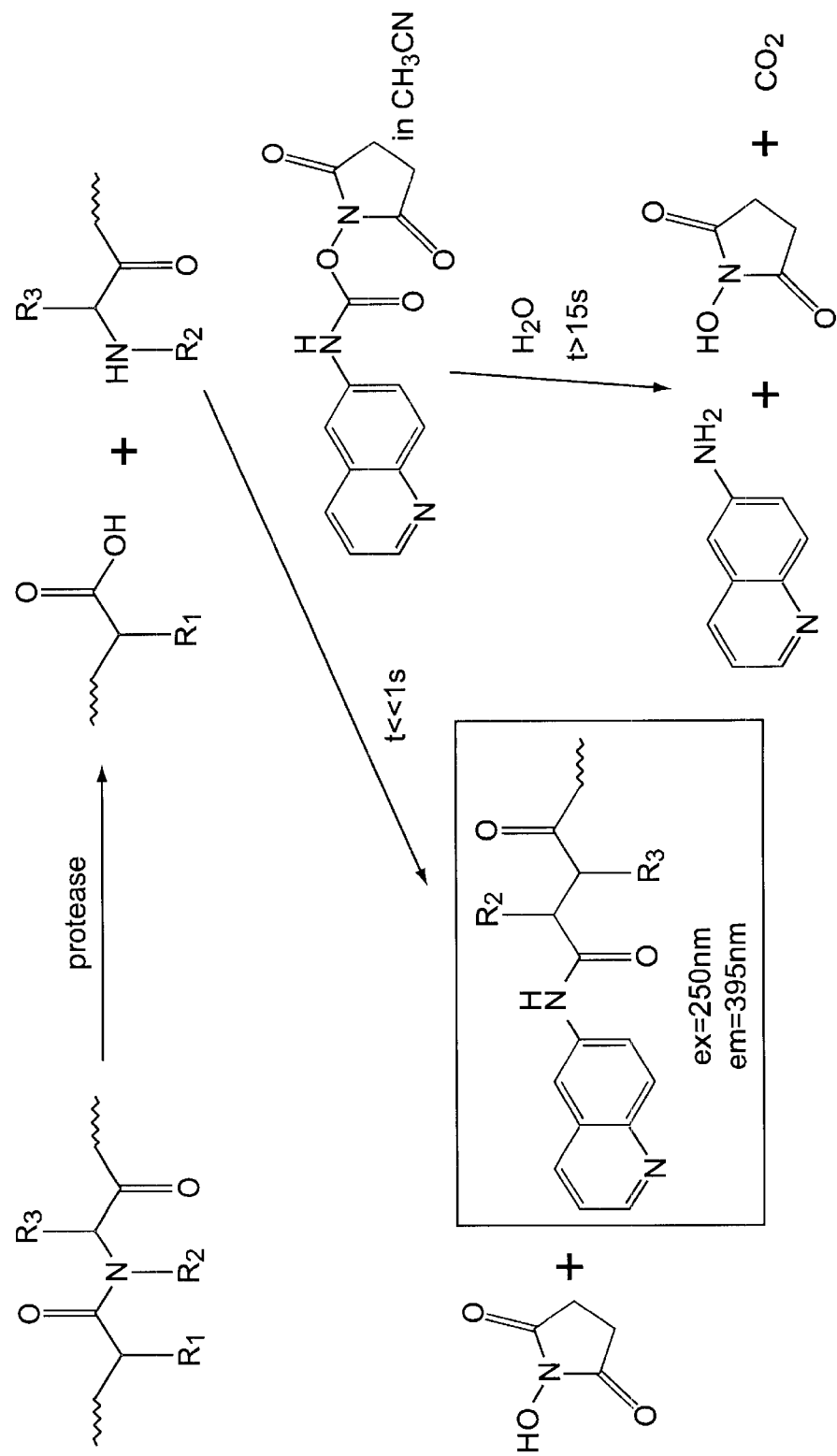
FIG. 5: An enzymatic protease reaction and the labeling reaction used to label the enzyme reaction products.

For example, 6-aminoquinolyl-N-hydroxysuccinimidyl carbamate converts both primary and secondary amino acids to stable fluorescent derivatives. The reaction, which is typically carried out by adding the reagent to and heating a buffered sample, occurs in a matter of seconds. The derivatives produced are easily separated, e.g., using reverse phase HPLC. Excess reagent is consumed during the reaction to form aminoquinoline, which has significantly different spectral properties than any of the derivatized amino acids. For example, highly stable urea derivatives fluoresce strongly at 395 nm. In a slower reaction, excess labeling reagent hydrolyzes to produce 6 aminoquinoline, N-hydroxysuccinimide, and carbon dioxide as shown in FIG. 5. The destruction of the excess reagent is complete within a minute. The major hydrolysis product, the aminoquinoline fluoresces weakly at 395 nm, producing a small peak that is easily resolved chromatographically. The carbon dioxide and N-hydroxysuccinimide do not interfere with the analysis. An example of the basic reaction is provided in FIG. 5.

Other useful labeling reagents in the present invention are aromatic dialdehydes which include, but are not limited to, o-pthaldialdehyde, napthalene-2-3-dicarboxaldehyde, anthracene-2,3-dicarboxaldehyde,a dn the like. Other aminederivatizing reagents include, but are not limited to, 3-(4-carboxybenzoylquinoline-2-carboxaldehyde, 3-(2-furosyl) quinoline-2-carboxaldehyde, fluorescamine, 7-nitrobenz-2-oxa-1,3-diazole chloride, and the like.

For example, fluorescamine and o-phthaldialdehyde are non-fluorescent reagents that react rapidly, e.g., on the order of seconds, with available primary amines to provide fluorescent amine derivatives. Fluorescamine reacts rapidly at alkaline pH to form a fluorescent substance. Free fluorescamine in the solution quickly hydrolyzes in an aqueous solution, in which the amine-derivative is not hydrolyzed. The aqueous solution in this case acts as an inactivating reagent to inactivate any unreacted fluorescamine so that it does not interfere with any remaining manipulations, assays, separations, and the like.

An "inactivating reagent" is one that is used to reduce interference from unreacted labeling reagents or by-products of the labeling reaction. Some unreacted labeling reagents and amine hydrolysis by-products share similar detection properties with the labeled products, e.g., fluorescently labeled products. To avoid potential interference in the detection step, the excess labeling reagents and by-products are optionally removed before separation and/or detection. Alternatively, the excess reagents and by-products are chromatographically resolved or separated from the selected peak, e.g., the peak corresponding to the labeled products, e.g., protease assay products.

In other embodiments, a labeling reagent is used that does not produce interfering by-products. For example, 6-aminoquinolyl-N-hydroxysuccininimydyl carbamate when used as a labeling reagent provides subpicomole detection limits. It has a shift in the emission maximum between the amino acid or peptide derivatives and the labeling reagent itself. Thus, excess reagent and hydrolysis products do not provide any substantial interference to the detection of the desired products.

Thus, the general methodology comprises forming the fluorescent derivatives using the labeling reagents as described above. Inactivating reagents are optionally used to insure that the derivatives formed are easily detectable. These fluorescent derivatives, e.g., protease assay products, are typically separated and detected. The separation step is preferably performed after the derivatization when the derivatives are stable, but a pre-separation is an option.

Separation of Components

The products of interest in the present invention are optionally separated either prior to or after the labeling reaction. Separating the products before the labeling step allows native species to be separated without any interference from the labeling reagent or the by-products. When the derivitization reactions occur after the separation, the derivitization chemistry is preferably a fast derivatization that maintains the integrity of the separation. Fluorescamine and o-phthalaldehyde are optionally used to perform post-separation labeling.

Alternatively, the derivatization reaction occurs before separation of the products. For example, products are first labeled and then separated in a system such as the one illustrated in FIG. 3. An assay is performed in main channel 302, producing products. The products are flowed into labeling region 304, to which a labeling reagent is added. The products and the labeling reagent react to form labeled products, which are then separated in separation channel 320 and optionally detected in detection channel region 306. For example a protease and a protein are introduced into main channel 302, where the protein is hydrolyzed into a variety of peptides and amino acids. The amino acids and peptides are labeled in labeling region 304, using 6-aminoquinolyl-N-hydroxysuccininimydyl carbamate, which is added from reservoir 314. The labeling reaction produces fluorescently labeled amino acids and peptides, which are then separated, e.g., electrophoretically, in separation channel 320.

Preferably, when performing labeling reactions prior to a separation step, the labeled products formed by the derivitization reaction are stable derivatives that do not degrade during the separation. For example, the labeling reagent 6-aminoquinolyl-N-hydroxysuccininimydyl carbamate produces stable derivatives that retain their integrity throughout the separation and detection steps.

The separation channels of the invention are optionally used to separate a variety of products, e.g., protease reaction products for detection purposes. A "mixture of components," as used herein, refers to a combination, known or unknown, of biological components, e.g., proteins, enzymes, carbohydrates, antibodies, peptides, polypeptides, amino acids, and the like. The components can be in a complex mixture, such as blood, serum, cell extracts, or in a purified solution, such as a buffered solution of amino acids. Alternatively, the separation column is used to separate excess labeling reagent from the labeled products or to separate labeling reaction by-products from the labeled products of interest.

When separating the products of a reaction or assay, the separation optionally occurs before or after the labeling step as discussed above. When separating excess labeling reagent or by-products from the labeled products, the separation is performed after the labeling step. In some embodiments, the products are optionally separated before labeling and then after labeling they are flowed through a second separation channel to separate out the by-products of the labeling reaction or the excess reagent.

Separation of components, e.g., products from other products or products from excess labeling reagent, is performed in a separation channel or region of the invention. Typically electrophoretic separation is used to separate the mixture of components in the sample. Electrophoretic separation is the separation of substances achieved by applying an electric field to samples in a solution or gel. In its simplest form, it depends on the different velocities with which the substances or components move in the field. The velocities depend, e.g., on the charge, mass, and size of the substances.

The separation channels or regions typically comprise a separation matrix. When the sample is flowed through the separation matrix, the components are separated, e.g., based on physical or chemical properties, such as molecular weight or charge. For example, peptides and polypeptides of varying sizes are optionally electrophoretically separated in the separation channels of the invention. Method of performing microfluidic separations are discussed in U.S. Pat. No. 5,948,227 issued Sep. 7, 1999, entitled "Methods and Systems for Performing Electrophoretic Molecular Separations," by Dubrow.

The separation matrix optionally comprises a polymer, a gel, or a solution. Alternatively, no separation medium is used to enhance electrophoretic separation. For example, buffer alone is optionally used. Preferably, the separation region, such as separation channel 320 in FIG. 3 or separation channel region 220 in FIG. 2, is a polyacrylamide gel filled channel, a polydimethylacrylamide, or a polydimethylacrylamide/co-acrylic acid polymer filled channel on which the mixture of components is electrophoretically separated based on charge/mass ratio or molecular weight. Other separation mediums used to enhance electrophoretic separation include, but are not limited to, linear polyacrylamide, cross-linked polyacrylamide, agarose, cellulose, silica gel, and the like. Alternatively, a buffer alone is used in the separation channel, e.g., in capillary electrophoresis. If the components are detected, e.g., by fluorescent labels provided by reacting products with the labeling reagents of the present invention, as they exit the separation region, the components are optionally identified by their retention times.

Other gel electrophoretic media that are optionally placed in a separation channel or region of the invention include silica gels such as Davisil Silica, E. Merck Silica Gel, Sigma-Aldrich Silica Gel (al available from Supelco) in addition to a wide range of silica gels available for various purposes as described in the Aldrich catalogue/handbook (Aldrich Chemical Company, Milwaukee, Wis.). Preferred gel materials include agarose based gels, various forms of acrylamide based gels (reagents available from, e.g., Supelco, SIGMA, Aldrich, Sigma-Aldrich and many other sources), colloidal solutions, such as protein colloids (gelatins) and hydrated starches. For a review of electrophoretic separation techniques and polyacrylamide gels, see, e.g., The Encyclopedia of Molecular Biology, Kendrew (ed.) (1994); and, Gel Electrophoresis of Proteins: A Practical Approach, $2^{nd}$ edition Hames and Rickwood (Eds.) IRL Press, Oxford England, (1990).

Other types of separation matrices are also optionally used and discussed in U.S. patent application Ser. No. 09/093,832 filed Jun. 8, 1998, entitled "Microfluidic Matric Localizations Apparatus and Methods," by Mehta and Kopf-Sill. Alternate separation matrix media include low pressure chromatography media, such as non-ionic macroreticular and macroporous resins which adsorb and release components based upon hydrophilic or hydrophobic interactions, e.g., Amberchrom and Amberlite resins (available from Supelco), Dowex, and Duolite (all available from Supelco). Other optional media include affinity media for purification and separation, such as acrylic beads, agarose beads, cellulose, sepharose, or the like. In addition, a wide variety of resins and chromatography media are also available, e.g., from Supelco, Sigma, Aldrich, or the like, for example, biotin resins, dye resins, aluminas, carbopacks, and the like. For a review of chromatography techniques and media, see, e.g., Affinity Chromatography- A Practical Approach, Dean et al., (Eds.) IRL Press, Oxford (1985); and, Chromatographic Methods, $5^{th}$ Edition, Braithwaite et al., (1996).

For example, a processed protein or polypeptide sample that has been desalted and denatured in SDS is optionally electrophoresed in a linear polyacrylamide gel filled separation channel containing SDS to separate the proteins and polypeptides on the basis of molecular weight of the subunits. A detector is optionally positioned so that it detects the proteins and/or polypeptides that are stained in the gel with a fluorescent protein stain. The retention time of the proteins as they are electrophoresed through the gel is used with markers to measure the molecular weight of the proteins.

After the labeling of the reaction products, the products are optionally detected. Detection optionally occurs right after the labeling reaction. However, if the labeling step is performed prior to separation then the products are typically detected as they elute from the separation region of the device.

Enzyme Kinetics

The above methods are optionally used to perform protease assays and, e.g., to obtain enzyme kinetic data, e.g., inhibition or activation rate constants for a variety of inhibitors. Determination of rate constants for reaction modulators, such as inhibition rate constants and activation rate constants, is performed by identifying the relation of the percentage of inhibition to inhibitor concentration for a given enzyme/catalyst and substrate/reactant concentration. The determination of kinetic relationships for reactants and other components in microfluidic systems has been described in various pending applications by the inventors and their coworkers.

For example, WO 98/56956 by Kopf-Sill et al., entitled "APPARATUS AND METHODS FOR CORRECTING FOR VARIABLE VELOCITY IN MICROFLUIDIC SYSTEMS," provides pioneering methods of obtaining kinetic information for moving reactants based, e.g., on the conservation of flux in microscale systems that use electrokinetic forces to move fluids.

In U.S. Ser. Nos. 60/142,984 and 09/609,030, both entitled "MICROFLUIDIC SYSTEMS AND METHODS FOR DETERMINING MODULATOR KINETICS" filed Jul. 6, 1999 and Jun. 30, 2000 respectively, Chow et al. provide for the use of signal information from one or a few samplings to produce kinetic information. The shape of a signal profile, e.g., from an enzymatic reaction, is deconvoluted to provide concentration dependence and kinetic information in real time. Calibration curves are optionally established to provide kinetic constants as a function of a dwell time or sip time, e.g., from a microwell plate. The data is then optionally used to direct any desired resampling. Additional sample volumes can be obtained from the same sample plate used for the initial screening, thus reducing throughput time.

These methods are optionally applied to signals obtained from the enzymatic reactions of the present invention to provide inhibition or activation rate constants. For example, a fluorescent signal from a peptide labeled by a reaction with 6-aminoquinolyl-N-hydroxysuccininimydyl carbamate is used to obtain kinetic data for the protease reaction that produced the peptide.

III. Devices and Integrated Systems

Although the devices and systems specifically illustrated herein are generally described in terms of the performance of a few or one particular operation, e.g., a protease assay, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include, but are not limited to, sample handling and preparation operations, e.g., cell separation, extraction, purification, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components, or the like. The devices and systems used for the above assays are described below.

Microfluidic Devices Generally

A variety of microscale systems are optionally adapted to the present invention by incorporating labeling regions and channels, separation channels, enzymes, substrates, labeling reagents, separation gels, and the like. Microfluidic devices which can be adapted to the present invention e.g., by the addition of a labeling reagent, e.g., an amine-derivatizing reagent, are described in various PCT applications and issued U.S. Patents by the inventors and their coworkers, including U.S. Pat. Nos. 5,699,157 (J. Wallace Parce) issued Dec. 16, 1997 U.S. Pat. No. 779,868 (J. Wallace Parce et al.) issued Jul. 14, 1998; U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998; U.S. Pat. No. 5,852,495 (J. Wallace Parce) issued Dec. 22, 1998, U.S. Pat. No. 5,869,004 (J. Wallace Parce et al.) issued Feb. 9, 1999; U.S. Pat. No. 5,876,675 (Colin B. Kennedy) issued Mar. 2, 1999, U.S. Pat. No. 5,880,071 (J. Wallace Parce et al.) issued Mar. 9, 1999 U.S. Pat. No. 5,882,465 (Richard J.

McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999; U.S. Pat. No. 5,958,203 (J. Wallace Parce et al.) issued Sep. 28, 1999, U.S. Pat. No. 5,958,694 (Theo T. Nikiforov) issued Sep. 28, 1999, and U.S. Pat. No. 5,959,291 (Morten J. Jensen) issued Sep. 28, 1999; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, and WO 99/44217.

For example, pioneering technology providing cell based microscale assays are set forth in U.S. Pat. No. 5,942,443, by Parce et al. "High Throughput Screening Assay Systems in Microscale Fluidic Devices" and, e.g., in No. 60/128,643 filed Apr. 4, 1999 and Ser. No. 09/510,626 filed Feb. 22, 2000, both entitled "Manipulation of Microparticles In Microfluidic Systems," by Mehta et al. Complete integrated systems with fluid handling, signal detection, sample storage and sample accessing are available. For example, U.S. Pat. No. 5,942,443 provides pioneering technology for the integration of microfluidics and sample selection and manipulation. Furthermore, additional applications have recently been filed describing improved methods for diluting samples, controlling fluid flow, and performing western type assays, e.g., U.S. Ser. No. 09/641,468 by Wada and Murphy, entitled "Microfluidic Analytic Detection Assays, Devices, and Integrated Systems," filed Aug. 17, 2000; and U.S. Ser. No. 09/645,104 by Kopf-Sill et al., entitled "Dilutions in High Throughput Systems with a Single Vacuum Source," filed Aug. 23, 2000.

In general, enzymes, substrates, modulators, labeling reagents, and other components can be flowed in a microscale system by electrokinetic (including either electroosmotic or electrophoretic) techniques, and/or using pressure-based flow mechanisms, or combinations thereof. For example pressure based flow is optionally used to flow a protease enzyme, a substrate, and an inhibitor into a main channel for a reaction and then electrophoretic flow control is used to separate the reaction products, e.g., a mixture of peptides and/or amino acids resulting from a proteolytic digestion of a protein.

Electrokinetic material transport systems or electrokinetic controllers are used in the present invention to provide movement of enzymes, substrates, modulators, and the like, through microfluidic channels. For example, the labeling reagents of the present invention are transported through the device, e.g., by electrokinetic material transport, to contact and react with the products to be labeled. "Electrokinetic material transport systems," as used herein, include systems that transport and direct materials within a microchannel and/or microchamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of proteins, enzymes, peptides, modulators, etc. suspended within the fluid. Similarly, the components, e.g., proteins, peptides, amino acids, enzymes, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis. For example, mixtures of peptides produced by a protease assay are electrophoretically separated based on mass/charge ratio in a channel comprising a separation polymer, gel, or matrix, such as a polyacrylamide solution.

Typically, the electrokinetic material transport and direction systems of the invention rely upon the electrophoretic mobility of charged species within the electric field applied to the structure. Such systems are more particularly referred to as electrophoretic material transport systems. For example, in the present system separation of a mixture of components into its individual components typically occurs by electrophoretic separation. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material that alters the surface charge of the channel.

A variety of electrokinetic controllers and systems which are optionally used in the present invention are described, e.g., in U.S. Pat. No. 5,858,195, by Ramsey issued Jan. 12, 1999, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled products in one or more channels toward a detection region or waste reservoir.

Particularly, modulation of the voltages applied at the various reservoirs, such as sources 110, 112, 108, 114, and the like in FIG. 1, can move and direct fluid flow through the interconnected channel structure of the device. For example, a voltage gradient applied between source 110 and a waste reservoir 118 will direct fluid through main channel 102. In addition, a voltage gradient applied between reservoirs 322 and 318 of FIG. 3 is optionally used to inject material at the intersection of main channel 302 and separation channel 320 into separation channel 320.

Other methods of transport are also available for situations in which electrokinetic methods are not desirable. For example, sample introduction and reaction are best carried out in a pressure-based system to avoid electrokinetic biasing during sample mixing and high throughput systems typically use pressure induced sample introduction. Pressure based flow is also desirable in systems in which electrokinetic transport is also used. For example, pressure based flow is optionally used for introducing and reacting reagents in a system in which the products are electrophoretically separated. In the present system, pressure based flow is optionally used to introduce and react the various reagents, e.g., a protease and a substrate, and electrophoretic flow control is typically used to separate the mixture of products produced from the substrate in a protease assay.

Pressure can be applied to microscale elements, e.g., to a channel, region, or reservoir, to achieve fluid movement using any of a variety of techniques. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe, or the like, to displace liquid and thereby raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In some embodiments, a vacuum source is applied to a reservoir or well at one end of a channel to draw a fluidic material through the channel. For example, a vacuum source is optionally placed at a reservoir in the present devices for drawing fluid into a channel, e.g., a vacuum source at reservoir 118 in FIG. 1 applies a pressure to main channel 102, thus drawing fluid into main channel 102, e.g., from reservoir 108, 112, or 110. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces are also optionally used to provide fluid pressure for continuous fluid flow of materials such as enzymes, substrates, modulators, or protein mixtures. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure. The capillary forces are optionally used in conjunction with the electrokinetic or pressure-based flow in the present invention. The capillary action pulls material through a channel. For example a wick is optionally added to, e.g., main channel 102, to aid fluid flow by drawing the reactants and/or products through the channel toward reservoir 118.

Mechanisms for reducing adsorption of materials during fluid-based flow are described in "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al., U.S. Ser. No. 09/310,027. In brief, adsorption of cells, components, proteins, enzymes, and other materials to channel walls or other microscale components during pressure-based flow can be reduced by applying an electric field such as an alternating current to the material during flow. For example, these mechanisms are optionally used in main channel 102 of FIG. 1 to maintain a continuous flow protease assay.

Mechanisms for focusing labeling reagents, enzymes, modulators, and other components into the center of microscale flow paths, which is useful in increasing assay throughput by regularizing flow velocity, e.g., in pressure based flow, is described in "FOCUSING OF MICROPARTICLES IN MICROFLUIDIC SYSTEMS" by H. Garrett Wada et al. U.S. Ser. No. 09/569,747, filed May 11, 2000. In brief, sample materials are focused into the center of a channel by forcing fluid flow from opposing side channels into the main channel comprising the cells, or by other fluid manipulations.

In an alternate embodiment, microfluidic systems are incorporated into centrifuge rotor devices, which are spun in a centrifuge. Fluids and particles travel through the device due to gravitational and centripetal/centrifugal pressure forces.

In addition to transport through the microfluidic system, the invention also provides for introduction of sample or reagents, e.g., enzymes, proteins, substrates, modulators, and the like, into the microfluidic system.

Sources of Assay Components and Integration with Microfluidic Formats

Reservoirs or wells are provided in the present invention as sources of samples, reagents, enzymes, substrates, buffers, and the like. Such wells include, e.g., reservoirs 112, 110, 108, 114, and 116 in FIG. 1. For example, a sample is optionally introduced into the device through reservoir 110. A labeling reagent is optionally contained within reservoir 114 and then introduced as desired into main channel 102. An inactivating reagent is optionally introduced from reservoir 116. An inactivating reagent is also optionally contained within the device, e.g., stored within one of the various reservoirs.

Sources of samples, mixtures of components, and reagents, e.g., enzymes, substrates, labeling reagents, and the like, are fluidly coupled to the microchannels noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in U.S. Ser. No. 09/510,626, filed Feb. 22, 2000, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others.

Figure 7:
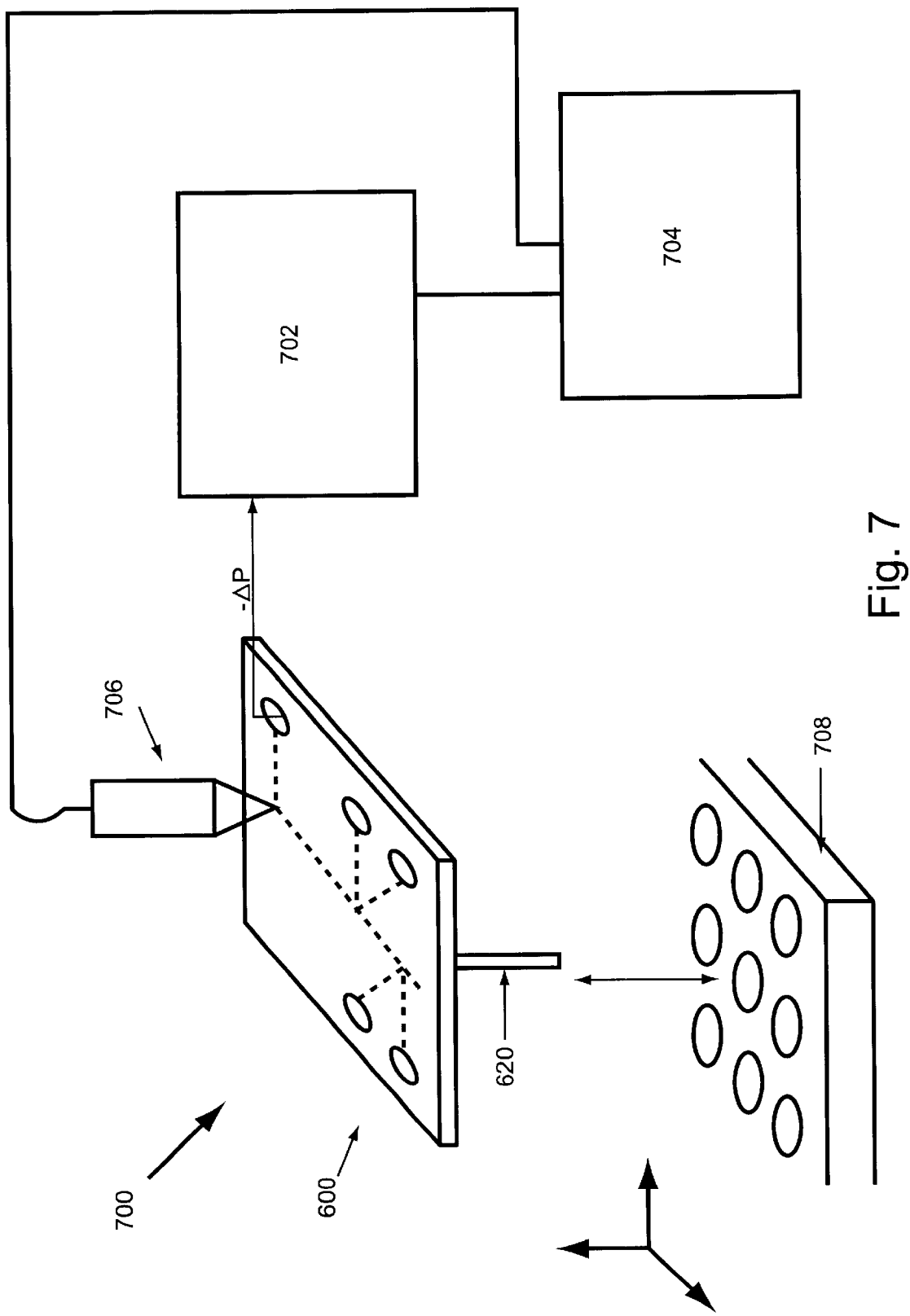

For example, the source of a sample, component, or buffer can be a microwell plate external to the body structure, having, e.g., at least one well with the selected sample, e.g., an potential protease inhibitor. For example, a microwell plate containing a plurality of potential inhibitors is optionally coupled to a pipettor channel as shown in FIGS. 6 and 7. The various inhibitors are drawn from the microwell plate into the pipettor channel and then into the microfluidic device, e.g., into main channel 604. In main channel 604 or another channel of the microfluidic device, the inhibitor sample is optionally tested to determine, e.g., activity and/or kinetic rate constants.

Alternative sources include a well disposed on the surface of the body structure comprising the sample, component, or reagent; a reservoir disposed within the body structure comprising the sample, component, mixture of components, or reagent; a container external to the body structure comprising at least one compartment comprising the sample, component, or reagent; or a solid phase structure comprising the sample or reagent in lyophilized or otherwise dried form.

A loading channel region is optionally fluidly coupled to a pipettor channel with a port external to the body structure.

The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

The integrated microfluidic system of the invention optionally includes a very wide variety of storage elements for storing samples and reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component, region, or channel of the microfluidic device using conventional robotics, or using an electropipettor or pressure pipettor channel fluidly coupled to a region or channel of the microfluidic system. Such reagents include, but are not limited to, labeling reagents, e.g., amine-derivatizing reagents, modulators, e.g., inhibitors or activators, enzymes, substrates, and the like.

The above devices, systems, features, and components are used in the integrated systems described below, e.g., to perform protease inhibition assays, to separate mixtures of products, to label products, and the like.

Instrumentation

In the present invention, materials, such as enzymes, proteins, antibodies, peptides, polypeptides, amino acids, and the like, are optionally monitored and/or detected so that presence of a product of interest can be detected or an activity or concentration can be determined. For example, in a protease inhibition assay, the amount of inhibition is determined by analysis of the amount of product formed in the assay. Kinetic rate constants are also optionally determined by the analysis of the products formed in the assay. The products are optionally labeled as described above and detected using the instrumentation and integrated systems described below. Depending on the label signal measurements, decisions are optionally made regarding subsequent fluidic operations, e.g., whether to assay a particular component or inhibitor in detail to determine, e.g., kinetic information.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Fluid Direction System

A variety of controlling instrumentation is optionally utilized in conjunction with the microfluidic devices described above, for controlling the transport and direction of fluidic materials and/or materials within the devices of the present invention, e.g., by pressure-based or electrokinetic control. For example, electrophoretic control systems are used to transport and separate reaction products in the separation channel region.

In the present system, the fluid direction system controls the transport, flow and/or movement of a sample through the microfluidic device. For example, the fluid direction system optionally directs the movement of the sample through a main channel, in which the sample is mixed and reacted with other reagents, e.g., in a protease assay. It optionally directs movement of a sample, an enzyme, and a substrate, e.g., an inhibitor, a protease, and a protein, into a main channel. Other reagents are also optionally added, e.g., buffers, salts, diluents, and the like. The reagents mix and/or react in the main channel. The fluid direction system also optionally directs the sample mixture and/or products produced by mixing and reacting into a labeling channel, in which the products are labeled as described above. Movement through the labeling channel region and into a separation region are also directed by the fluid direction system. For example, the products of an enzyme reaction are optionally separated before or after the labeling step. The fluid direction system directs the transport of the products into a separation channel region or a labeling region depending, as discussed above, on the type of assay and labeling reagent used.

For example, in many cases, fluid transport and direction are controlled, in whole or in part, using pressure based flow systems that incorporate external or internal pressure sources to drive fluid flow. For example, samples are optionally introduced into the system using a pressure based flow control.

Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357.

Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999 by Chow and Parce, entitled "Devices, Systems and Methods for Time Domain Multiplexing of Reagents".

Alternatively, electrokinetic controllers are used to apply voltage gradients across channel systems, thus transporting components, e.g., charged components through the channels. For example, enzyme assay products are typically separated electrophoretically using electrokinetic controllers to control the voltages applied to the separation channel.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

Detection System

The devices herein optionally include signal detectors, e.g., which detect fluorescence, phosphorescence, radioactivity, pH, charge, absorbance, luminescence, temperature, magnetism, color, or the like. Fluorescent detection is especially preferred. For example, the labeling reagents of the present invention react with unlabeled products or components to produce fluorescently labeled products or components. These components are then detectable using fluorescent detection systems.

The detector(s) optionally monitors one or a plurality of signals from downstream of the labeling region or the separation region in which the products of interest, e.g., a mixture of peptides, have optionally been labeled and separated. For example, the detector optionally monitors an optical signal that corresponds to a labeled component, such as a labeled polypeptide located, e.g., in detection region 206 in FIG. 2. In another embodiment, the detector monitors a plurality of optical signals, which correspond in position to various separated components, e.g., polypeptides that have been separated by weight. In another embodiment, the detector is positioned at the downstream end of a separation region or channel and detects a plurality of signals from separated components as they elute from a separation matrix.

Peptides, polypeptides, amino acids, protein fragments, or other components which emit a detectable signal are optionally flowed through a detection region of the invention. For example, the labeled products of the present invention emit a detectable fluorescent signal. A detector is placed proximal to the detection region and the labeled components are detected as they flow past the detector. The signal obtained is used to obtain, e.g., concentration and kinetic data. Alternatively, the detector can move relative to the device to determine the position of a protein, peptide, or the like (or, the detector can simultaneously monitor a number of spatial positions corresponding to channel regions, e.g., as in a CCD array).

The detector optionally includes or is operably linked to a computer, e.g., which has software for converting detector signal information into assay result information, e.g., molecular weight based on retention time or elution time, concentration of a polypeptide, peptide, amino acid, inhibition rate constants, activation rate constants, or the like. In addition, sample signals are optionally calibrated, e.g., by calibrating the microfluidic system by monitoring a signal from a known source.

A microfluidic system can also employ multiple different detection systems for monitoring the output of the system. Detection systems of the present invention are used to detect and monitor the materials in a particular channel region (or other detection region). Once detected, the flow rate and velocity of cells in the channels is also optionally measured and controlled.

Typically, the detector in the present invention is an optical detector, e.g., a fluorescence detector, that detects products, which have been labeled as described above. Other types of labeling reactions are also optionally carried out in-line in the microfluidic devices as described above, e.g., chemiluminescence derivatives are optionally added to assay products. Appropriate types of sensors are readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems of the present invention are optical detection systems for detecting an optical property of a material within the channels and/or chambers of the microfluidic provided herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials' spectral characteristics. In preferred aspects, the detector measures an amount of light emitted from the material, such as from a fluorescent or chemiluminescent material, e.g., the labeled products described above. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as the labeled products produced by the methods of the present invention, the detector typically includes a light source which produces light at an appropriate wavelength for activating the fluorescent material, as well as optics for directing the light source through the detection window to the product contained in the channel or chamber. The light source can be any number of light sources that provides an appropriate wavelength, including lasers, laser diodes and LEDs. Other light sources are required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the fluid direction system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. For example, the software optionally directs the fluid direction system to transport enzymes, substrates, and inhibitors into a main channel, products of the enzymatic reaction into a labeling region, labeled products into a separation channel, and any other movement necessary to analyze the results of the assay performed.

The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like. For example, the voltages on an electrophoretic separation channel are optionally adjusted.

In addition, the computer optionally includes software for deconvolution of the signal or signals from the detection system. For example, a deconvolution of the data provides molecular weights and concentrations of the various peptides, polypeptides and amino acids detected. In addition, instruction sets are optionally included for deconvoluting the data as described in WO 98/56956 and U.S. Ser. No. 09/609,030 to obtain kinetic rate constants.

Example Integrated System

FIG. 6, Panels A, B, and C and FIG. 7 provide additional details regarding example integrated systems that are optionally used to practice the methods herein. As shown, body structure 602 has main channel 604 disposed therein. For example, an inhibitor sample is optionally flowed from pipettor channel 620 towards reservoir 614, e.g., by applying a vacuum at reservoir 614 (or another point in the system) or by applying appropriate voltage gradients. Alternatively, a vacuum is applied at reservoirs 606, 608, 612 or through pipettor channel 620. Enzymes and substrates are optionally flowed into main channel 604 from reservoirs 608 and 606. The enzymes and substrates react in main channel 604 and produce products. A labeling reagent is added into main channel 604 from reservoir 610. The labeling reagent mixes with and reacts with the products from the enzymatic reaction and produces labeled products. An inactivating reagent is optionally flowed from reservoir 612 into main channel 604 to inactivate any unreacted or excess labeling reagent. The materials are then flowed through main channel 604 toward a detection region. A separation channel region is optionally included within main channel 604 or as an additional channel. Additional materials, such as buffer solutions, diluents, and the like, as described above are optionally flowed from wells 610 or 612 and into main channel 604. Flow from these wells is optionally performed by modulating fluid pressure, or by electrokinetic approaches as described (or both). The arrangement of channels depicted in FIG. 6 is only one possible arrangement out of many which are appropriate and available for use in the present invention. For example, a few alternatives are provided in FIGS. 1, 2, and 3.

Samples and materials are optionally flowed from the enumerated wells or from a source external to the body structure. As depicted, the integrated system optionally includes pipettor channel 620, e.g., protruding from body 602, for accessing a source of materials external to the microfluidic system. Typically, the external source is a microtiter dish or other convenient storage medium. For example, as depicted in FIG. 7, pipettor channel 620 can access microwell plate 708, which includes sample materials, component-binding moieties, wash solutions, blocking solutions, and the like, in the wells of the plate.

Detector 706 is in sensory communication with channel 704, detecting signals resulting, e.g., from labeled products. Detector 706 is optionally coupled to any of the channels or regions of the device where detection is desired. Detector 706 is operably linked to computer 704, which digitizes, stores, and manipulates signal information detected by detector 706, e.g., using any of the instructions described above, e.g., or any other instruction set, e.g., for determining retention time, molecular weight or identity.

Fluid direction system 702 controls voltage, pressure, or both, e.g., at the wells of the systems or through the channels of the system, or at vacuum couplings fluidly coupled to channel 604 or other channel described above. Optionally, as depicted, computer 704 controls fluid direction system 702. In one set of embodiments, computer 704 uses signal information to select further parameters for the microfluidic system. For example, upon detecting the presence of a protease assay product, the computer optionally directs addition of a labeling reagent into the system.

Kits

Generally, the microfluidic devices described herein are optionally packaged to include reagents for performing the device's preferred function. For example, the kits optionally include any of microfluidic devices described along with assay components, reagents, sample materials, proteins, antibodies, particle sets, control materials, or the like. For example a protease inhibition assay kit typically includes a protease, a protease substrate, e.g., a protein, and a labeling reagent such as 6-aminoquinolyl-N-hydroxysuccinimidyl carbamate. Inactivating reagents are also typically included. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like. Kits also optionally include packaging materials or containers for holding microfluidic device, system or reagent elements.

The discussion above is generally applicable to the aspects and embodiments of the invention described in the claims. Moreover, modifications can be made to the method and apparatus described herein without departing from the spirit and scope of the invention as claimed, and the invention can be put to a number of different uses.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of performing a protease assay in a microfluidic system, the method comprising:
   (i) flowing a protease through at least one microscale cavity;
   (ii) contacting the protease with a protease substrate in the at least one microscale cavity or an additional microscale cavity, thereby reacting the protease substrate with the protease and producing one or more products;
   (iii) labeling the one or more products by flowing a labeling reagent into the at least one microscale cavity or into the additional microscale cavity to react with the one or more products and produce one or more labeled products.

2. The method of claim 1, wherein the one or more products comprise at least one unlabeled amino acid, peptide, or protein.

3. The method of claim 1, wherein the labeling reagent comprises a chemically reactive labeling reagent.

4. The method of claim 1, wherein the labeling reagent comprises an amine-derivatizing reagent.

5. The method of claim 4, wherein the amine-derivatizing reagent comprises a non-fluorescent reagent prior to reacting the labeling reagent with the one or more products.

6. The method of claim 1, wherein the labeling reagent comprises a heterocyclic aromatic carbamate compound.

7. The method of claim 6, wherein the heterocyclic aromatic carbamate compound is 6-aminoquinolyl-N-hydroxysuccinimidyl carbamate.

8. The method of claim 6, wherein the heterocyclic aromatic carbamate compound is selected from: 3-aminoquinolyl-N-hydroxysuccinimidyl carbamate, 5-aminoquinolyl-N-hydroxysuccinimidyl carbamate, 5-aminoisoquinolyl-N-hydroxysuccinimidyl carbamate, 6-amino-4-methylquinolyl-N-hydroxysuccinimidyl carbamate, 6-amino-2,4-dimethylquinolyl-N-hydroxysuccinimidylcarbamate, 6-amino-2phenylquinolyl-N-hydroxysuccinimidyl-carbamate, 6-amino-2-methoxy-4-methylquinolyl-N-hydroxysuccinimidylcarbamate, 4-aminoquinaldine-N-hydroxysuccinimidyl carbamate, 9-aminoacridine-N-hydroxysuccinimidyl carbamate, 2-aminoacridine-N-hydroxysuccinimidylcarbamate, luminol-N-hydroxysuccinimidylcarbamate, isoluminol-N-hydroxysuccinimidylcarbamate, 7-amino4-methylcoumarin-N-hydroxysuccinimidylcarbamate, 7-amino-4-(trifluoromethyl)coumarin-N-hydroxysuccinimidylcarbamate, 4'-(aminomethyl)fluorescein-N-hydroxysuccinimidylcarbamate, 5-(aminomethyl)fluorescein-N-hydroxysuccinimidylcarbamate, 5-aminoeosin-N-hydroxysuccinimidylcarbamate, and Cascade Blue ethylenediamine-N-hydroxysuccinimidylcarbamate.

9. The method of claim 4, wherein the labeling reagent comprises 3-(4-carboxybenzoylquinoline-2-carboxaldehyde, 3-(2-furosyl) quinoline-2-carboxaldehyde, fluorescamine, or 7-nitrobenz-2-oxa-1,3-diazole chloride.

10. The method of claim 4, wherein the labeling reagent comprises an aromatic dialdehyde.

11. The method of claim 10, wherein the aromatic dialdehyde is selected from: o-pthaldialdehyde, napthalene-2-3-dicarboxaldehyde, and anthracene-2,3-dicarboxaldehyde.

12. The method of claim 1, wherein the labeling step comprises chemically reacting the labeling reagent with the one or more products.

13. The method of claim 1, comprising flowing one or more of: the protease, the protease substrate, the one or more products, the one or more labeled products, and the labeling reagent, through the microfluidic system by applying pressure or electrokinetic forces to one or more of: the protease, the protease substrate, the one or more products, the one or more labeled products, and the labeling reagent, in the microfluidic system.

14. The method of claim 1, further comprising separating the one or more products or the one or more labeled products in the microscale cavity or in the additional microscale cavity.

15. The method of claim 14, wherein the separating comprises electrophoretically separating the one or more products or the one or more labeled products in a polymer, a gel, or a solution.

16. The method of claim 15, wherein the polymer, gel, or solution comprises polyacrylamide, linear polyacrylamide, cross-linked polyacrylamide, polydimethylacrylamide, polydimethylacrylamide/co-acrylic acid, agarose or cellulose.

17. The method of claim 1, further comprising flowing an inactivating reagent through the at least one microscale cavity or the additional microscale cavity after the labeling step, thereby inactivating any labeling reagents that have not reacted with the one or more products.

18. The method of claim 17, wherein flowing an inactivating reagent through the at least one microscale cavity or the additional microscale cavity comprises altering the pH of the enzyme, the substrate, the products, or the labeled products.

19. The method of claim 1, further comprising contacting the enzyme and substrate with one or more modulators.

20. The method of claim 19, wherein the one or more modulators comprise at least one inhibitor or at least one activator.

21. The method of claim 1, further comprising providing a detection system and detecting the one or more labeled products with the detection system.

22. The method of claim 21, wherein detecting comprises fluorescently detecting the one or more labeled products.

23. The method of claim 21, further comprising providing a computer, operably coupled to the detection system, the computer comprising software, which software comprises at least a first instruction set, which first instruction set quantitates the amount of the one or more labeled products detected by the detection system.

24. A method of labeling one or more products in a microfluidic system, the method comprising:
   (i) flowing one or more unlabeled components through at least one microfluidic cavity;
   (ii) reacting the one or more unlabeled components with one or more unlabeled reagents in the at least one microscale cavity or in an additional microscale cavity, resulting in one or more unlabeled products; and,
   (iii) labeling the one or more unlabeled products by flowing a heterocyclic aromatic carbamate compound into contact with the one or more unlabeled products in the at least one microscale cavity or in the additional microscale cavity, thereby reacting the heterocyclic aromatic carbamate compound with the one or more unlabeled products and producing one or more labeled products.

25. A microfluidic device for in-line labeling, the device comprising a body structure having a plurality of microscale channels disposed therein, the plurality of channels comprising:
- (i) a main channel; in which main channel at least one protease and at least one protease substrate are reacted to produce one or more unlabeled products;
- (ii) a labeling channel region fluidly coupled to the main channel; in which labeling channel region the one or more unlabeled products are labeled to produce one or more labeled products;
- (iii) a detection channel region fluidly coupled to the main channel, in which detection channel region the one or more labeled products are detected;
- (iv) at least a first source fluidly coupled to the main channel, which first source comprises an amine-derivatizing reagent, which reagent reacts with the one or more unlabeled products to produce the one or more labeled products.

26. The device of claim 25, wherein at least one of the one or more unlabeled products comprises an unlabeled protein, a peptide, or an amino acid.

27. The device of claim 25, wherein the amine-derivatizing reagent is a heterocyclic aromatic carbamate compound.

28. The device of claim 27, wherein the heterocyclic aromatic carbamate compound comprises 6-aminoquinolyl-N-hydroxysuccinimidyl carbamate.

29. The device of claim 27, wherein the heterocyclic aromatic carbamate compound is selected from: 3-aminoquinolyl-N-hydroxysuccinimidyl carbamate, 5-aminoquinolyl-N-hydroxysuccinimidyl carbamate, 5-aminoisoquinolyl-N-hydroxysuccinimidyl carbamate, 6-amino-4-methylquinolyl-N-hydroxysuccinimidyl carbamate, 6-amino-2,4-dimethylquinolyl-N-hydroxysuccinimidylcarbamate, 6-amino-2phenylquinolyl-N-hydroxysuccinimidyl-carbamate, 6-amino-2-methoxy-4-methylquinolyl-N-hydroxysuccinimidylcarbamate, 4-aminoquinaldine-N-hydroxysuccinimidyl carbamate, 9-aminoacridine-N-hydroxysuccinimidyl carbamate, 2-aminoacridine-N-hydroxysuccinimidylcarbamate, luminol-N-hydroxysuccinimidylcarbamate, isoluminol-N-hydroxysuccinimidylcarbamate, 7-amino4-methylcoumarin-N-hydroxysuccinimidylcarbamate, 7-amino-4-(trifluoromethyl)coumarin-N-hydroxysuccinimidylcarbamate, 4'-(aminomethyl)fluorescein-N-hydroxysuccinimidylcarbamate, 5-(aminomethyl)fluorescein-N-hydroxysuccinimidylcarbamate, 5-aminoeosin-N-hydroxysuccinimidylcarbamate, and Cascade Blue ethylenediamine-N-hydroxysuccinimidylcarbamate.

30. The device of claim 25, wherein the amine-derivatizing reagent comprises 3-(4-carboxybenzoylquinoline-2-carboxaldehyde, 3-(2-furosyl)quinoline-2-carboxaldehyde, fluorescamine, or 7-nitrobenz-2-oxa-1,3-diazole chloride.

31. The device of claim 25, wherein the amine-derivatizing reagent comprises an aromatic dialdehyde.

32. The device of claim 31, wherein the aromatic dialdehyde is selected from: o-pthaldialdehyde, napthalene-2-3-dicarboxaldehyde, and anthracene-2,3-dicarboxaldehyde.

33. The device of claim 25, wherein the device further comprises at least a second source, which second source comprises a protease.

34. The device of claim 25, wherein the device further comprises at least a second source, which second source comprises a protease substrate.

35. The device of claim 25, wherein the device further comprises a second source, which second source comprises an inactivating reagent.

36. The device of claim 35, wherein the inactivating reagent alters the pH of one or more of: the protease, the protease substrate, the unlabeled products, and the labeled products.

37. The device of claim 25, the device further comprising a separation channel region for separating the one or more unlabeled products or the one or more labeled products, which separation channel region is fluidly coupled to the main channel.

38. The device of claim 37, wherein the separation channel region comprises a polymer, gel, or solution.

39. The device of claim 38, wherein the polymer, gel, or solution comprises polyacrylamide or polydimethylacrylamide/co-acrylic acid.

40. A system for performing in-line labeling in a microfluidic device, the system comprising:
- (i) a microfluidic device comprising a plurality of microscale channels disposed therein, the plurality of microscale channels comprising:
  - (a) a main channel; in which main channel at least one protease and at least one protease substrate are reacted to produce one or more unlabeled products;
  - (b) a labeling channel region fluidly coupled to the main channel; in which labeling channel region the one or more unlabeled products are labeled to produce one or more labeled products;
  - (c) a detection channel region fluidly coupled to the main channel, in which detection channel region the one or more labeled products are detected;
  - (d) at least a first source fluidly coupled to the main channel, which first source comprises an amine-derivatizing reagent, which reagent reacts with the one or more unlabeled products to produce the one or more labeled products;
- (ii) a fluid direction system fluidly coupled to the microfluidic device, which fluid direction system transports one or more of: the at least one protease, the at least one protease substrate, the one or more unlabeled products, the one or more labeled products, and the amine-derivatizing reagent, through the plurality of microscale channels;
- (iii) a control system operably linked to the fluid direction system, which control system instructs the fluid direction system to transport one or more of: the at least one protease, the at least one protease substrate, the one or more unlabeled products, the one or more labeled products, and the amine-derivatizing reagent, through the plurality of microscale channels; and,
- (iv) a detection system positioned proximal to the detection channel region for detecting the one or more labeled products.

41. The system of claim 40, wherein the fluid direction system transports one or more of: the at least one protease, the at least one protease substrate, the one or more unlabeled products, the one or more labeled products, and the amine-derivatizing reagent, through the plurality of microscale channels by applying pressure or electrokinetic forces to one or more of: the at least one protease, the at least one protease substrate, the one or more unlabeled products, the one or more labeled products, and the amine-derivatizing reagent.

42. The system of claim 40, the system further comprising a computer operably coupled to the system, and software, which software comprises at least a first instruction set.

43. The system of claim 42, wherein the first instruction set analyzes signals produced from the detection system.

44. The system of claim 42, wherein the first instruction set quantitates signals produced from the detection system.

45. The system of claim 42, wherein the first instruction set directs fluid movement in the system.

46. The system of claim 45, wherein the first instruction set directs the at least one protease and the at least one protease substrate to flow through the main channel; directs the amine-derivatizing reagent to flow into contact with the one or more unlabeled products in the labeling channel region, thereby producing labeled products; and directs the movement of the labeled products through the detection channel region.

* * * * *